United States Patent [19]

Eckhardt et al.

[11] Patent Number: 4,533,659
[45] Date of Patent: Aug. 6, 1985

[54] MICROBICIDAL 2-(1H-1,2,4-TRIAZOLYLMETHYL-1'-YL)-2-SILOXY-2-PHENYL-ACETATES

[75] Inventors: Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 499,725

[22] Filed: May 31, 1983

[30] Foreign Application Priority Data

Sep. 6, 1982 [CH] Switzerland ............ 3558/82

[51] Int. Cl.³ .................. A61K 31/555; C07D 207/30
[52] U.S. Cl. ...................................... 514/184; 548/101; 548/262
[58] Field of Search ............... 548/101, 262; 424/245, 424/269; 71/88

[56] References Cited

U.S. PATENT DOCUMENTS 4,005,083  1/1977  Büchel et al. ............ 424/269
4,291,044  9/1981  Jäger et al. .............. 424/245
4,366,152 12/1982  Krämer et al. ........... 548/101

FOREIGN PATENT DOCUMENTS 86173  8/1983  European Pat. Off. ........... 548/262

OTHER PUBLICATIONS

Eckhardt et al., Chem. Abst. 101: 7423c.

Primary Examiner—Donald G. Daus
Assistant Examiner—Cecilia Shen
Attorney, Agent, or Firm—Edward McC. Roberts; Frederick H. Rabin

[57] ABSTRACT

The invention relates to microbicidal silyloxyalkane azoles of the formula I

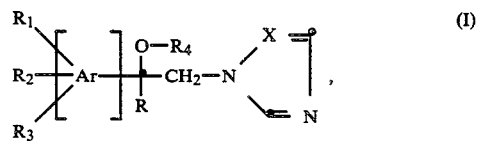

wherein
X is the bridge member —CH= or —N=,
Ar is a phenyl, diphenyl or naphthyl group,
$R_1$, $R_2$ and $R_3$ independently of one another are hydrogen, nitro, halogen, $C_1$-$C_3$alkyl, $C_1$-$C_3$alkoxy or $C_1$-$C_3$haloalkyl, R is one of the groups —$COOR_5$, —$COSR_6$,

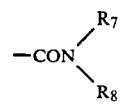

or —CN, $R_5$ is $C_2$-$C_{10}$alkenyl which is unsubstituted or substituted by halogen; $C_2$-$C_{10}$alkynyl which is unsubstituted or substituted by halogen; or is a $C_3$-$C_8$cycloalkyl group or a phenyl group which is unsubstituted or substituted by halogen, $C_1$-$C_4$alkyl, $C_1$-$C_4$alkoxy, —CN or —$CF_3$; or is a $C_1$-$C_{12}$alkyl chain which from $C_2$alkyl may be interrupted by oxygen or sulfur and is unsubstituted or substituted by a member selected from the group consisting of halogen, phenyl, —COO—$C_1$—$C_4$alkyl, —CO—$C_1$—$C_4$alkyl, —CO—phenyl, an unsaturated or saturated 5- or 6-membered ring containing oxygen or sulfur as heteroatom, with each phenyl moiety being unsubstituted or substituted by one or more identical or different halogen atoms, $R_6$ is $C_1$-$C_{10}$alkyl, or is a phenyl or benzyl group, each unsubstituted or substituted by halogen, $C_1$-$C_4$alkyl, $C_1$-$C_4$alkoxy, —CN or —$CF_3$, $R_7$ and $R_8$, each independently of the other, are hydrogen, $C_1$-$C_6$alkyl, $C_3$-$C_7$cycloalkyl, or a phenyl or benzyl group in each of which the aromatic ring is unsubstituted or substituted by halogen, $C_1$-$C_4$-alkyl, $C_1$-$C_4$alkoxy, —CN or —$CF_3$, or one of $R_7$ and $R_8$ is also the —N($R_9$)($R_{10}$) group or both taken together form a 5- or 6-membered saturated or unsaturated heterocyclic ring which may additionally contain 1 or 2 further N atoms, $R_9$ and $R_{10}$, each independently of the other, are hydrogen, $C_1$-$C_4$alkyl or a phenyl radical which is unsubstituted or substituted by halogen, $C_1$-$C_4$alkyl, —CN or —$CF_3$; and $R_4$ is the —Si($R_{11}$)($R_{12}$)($R_{13}$) group, wherein each of $R_{11}$, $R_{12}$ and $R_{13}$ independently is a radical selected from $C_1$-$C_4$alkyl, $C_3$-$C_7$alkenyl or phenyl, each unsubstituted or substituted by one or more halogen atoms, and the acid addition salts and metal complexes thereof.

Also disclosed are methods of preparing these compounds and also pesticidal compositions which contain at least one of the novel compounds as active ingredient. A method of controlling phytopathogenic microorganisms with the aid of the novel compounds of the invention is also described.

8 Claims, No Drawings

MICROBICIDAL 2-(1H-1,2,4-TRIAZOLYLMETHYL-1'-YL)-2-SILOXY-2-PHENYL-ACETATES

The present invention relates to silyloxyalkane azoles of the formula I below and to the agriculturally acceptable acid addition salts and metal complexes thereof. The invention further relates to the preparation of these compounds as well as to agrochemical compositions which contain at least one of the novel compounds as active ingredient. The invention also relates to the preparation of such compositions and to a method of controlling harmful microorganisms or of treating plants to prevent them from attack by such microorganisms.

Accordingly, the invention relates to compounds of the formula I

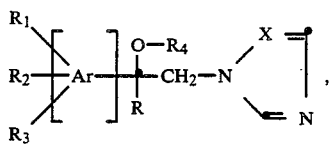

wherein

X is the bridge member —CH= or —N=,

Ar is a phenyl, diphenyl or naphthyl group, $R_1$, $R_2$ and $R_3$ independently of one another are hydrogen, nitro, halogen, $C_1$–$C_3$alkyl, $C_1$–$C_3$alkoxy or $C_1$–$C_3$haloalkyl, R is one of the groups —COOR$_5$, —COSR$_6$,

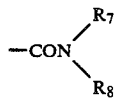

or —CN, $R_5$ is $C_2$–$C_{10}$alkenyl which is unsubstituted or substituted by halogen; $C_2$–$C_{10}$alkynyl which is unsubstituted or substituted by halogen; or is a $C_3$–$C_8$cycloalkyl group or a phenyl group which is unsubstituted or substituted by halogen, $C_1$–$C_4$alkyl, $C_1$–$C_4$alkoxy, —CN or —CF$_3$; or is a $C_1$–$C_{12}$alkyl chain which from $C_2$alkyl may be interrupted by oxygen or sulfur and is unsubstituted or substituted by a member selected from the group consisting of halogen, phenyl, —COO—$C_1$–$C_4$alkyl, —CO—$C_1$–$C_4$alkyl, —CO-phenyl, an unsaturated or saturated 5- or 6-membered ring containing oxygen or sulfur as heteroatom, with each phenyl moiety being unsubstituted or substituted by one or more identical or different halogen atoms, $R_6$ is $C_1$–$C_{10}$alkyl, or is a phenyl or benzyl group, each unsubstituted or substituted by halogen, $C_1$–$C_4$alkyl, $C_1$–$C_4$alkoxy, —CN or —CF$_3$, $R_7$ and $R_8$, each independently of the other, are hydrogen, $C_1$–$C_6$alkyl, $C_3$–$C_7$cycloalkyl, or a phenyl or benzyl group in each of which the aromatic ring is unsubstituted or substituted by halogen, $C_1$–$C_4$-alkyl, $C_1$–$C_4$alkoxy, —CN or —CF$_3$, or one of $R_7$ and $R_8$ is also the —N(R$_9$)(R$_{10}$) group or both taken together form a 5- or 6-membered saturated or unsaturated heterocyclic ring which may additionally contain 1 or 2 further N atoms, $R_9$ and $R_{10}$, each independently of the other, are hydrogen, $C_1$–$C_4$alkyl or a phenyl radical which is unsubstituted or substituted by halogen, $C_1$–$C_4$alkyl, —CN or —CF$_3$; and $R_4$ is the —Si(R$_{11}$)(R$_{12}$)(R$_{13}$) group, wherein each of $R_{11}$, $R_{12}$ and $R_{13}$ independently is a radical selected from $C_1$–$C_4$alkyl, $C_3$–$C_7$alkenyl or phenyl, each unsubstituted or substituted by one or more halogen atoms, and the acid addition and metal complexes thereof.

Depending on the number of indicated carbon atoms, alkyl by itself or as moiety of another substituent comprises e.g. the following groups: methyl, ethyl, propyl, butyl, pentyl, hexyl, heptyl, octyl, nonyl, decyl, undecyl or dodecyl, and the isomers thereof, e.g. isopropyl, isobutyl, tert-butyl, isopentyl etc. Alkenyl is e.g. vinyl, propen-1-yl, allyl, buten-1-yl, buten-2-yl, buten-3-yl etc., as well as chains containing several double bonds. Alkynyl is e.g. propyn-1-yl, propargyl, butyn-1-yl, butyn-2-yl etc., with propargyl being preferred. Haloalkyl is in particular a monohalogenated to perhalogenated alkyl substituent, e.g. CHCl$_2$, CH$_2$Cl, CCl$_3$, CF$_3$, CH$_2$CH$_2$Cl etc. Throughout this specification, halogen denotes fluorine, chlorine, bromine or iodine, with chlorine, bromine or fluorine being preferred. Cycloalkyl is e.g. cyclopropyl, cyclobutyl, cyclopentyl, cyclohexyl, or cycloheptyl, with cyclopropyl and cyclohexyl being preferred. Haloalkenyl is an alkenyl group which is substituted by one or more halogen atoms, e.g. chlorine and bromine, preferably chlorine. Furyl is preferably 2-furyl, tetrahydrofuryl, preferably 2-tetrahydrofuryl. Pyridyl is preferably pyrid-3- or -4-yl. Naphthyl is α- or β-naphthyl, preferably α-naphthyl. Examples of heterocyclic 5- or 6-membered rings containing up to 3 nitrogen atoms are pyrazole, imidazole, 1,2,4-triazole and 1,3,4-triazole, pyridine, pyrazine, pyrimidine, pyridazine, 1,3,5-triazine and 1,2,4-triazine.

Examples of salt-forming acids are inorganic acids, e.g. hydrohalic acids such as hydrofluoric acid, hydrochloric acid, hydrobromic acid, or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals may exist in different valency states. The metal complexes of the formula I may be mononuclear or polynuclear, i.e. they can contain one or more parts of the organic molecule is ligands. Complexes with copper, znc, manganese and tin are preferred.

The compounds of formula I are oils, resins or mainly solids which are stable at room temperature and have very valuable microbicidal properties. They can be used in agriculture or related fields preventively and curatively for controlling phytopathological microorganisms, for which utility the triazolylmethyl derivatives falling within the scope of formula I (X is N) are preferred. The compounds of formula I are very well tolerated by cultivated plants. The development of the plants is not impeded or retarded in any stage.

An important and preferred subgroup of compounds of the formula I comprises those of the formula I*

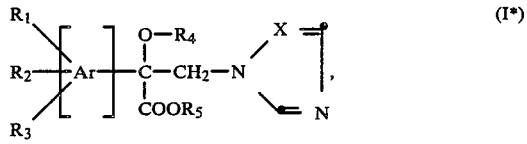

wherein
X is the bridge member —CH= or —N=,
Ar is a phenyl, diphenyl or naphthyl group,
$R_1$, $R_2$ and $R_3$, each independently of the other, are hydrogen, nitro, halogen, $C_1$-$C_3$alkyl, $C_1$-$C_3$alkoxy or $C_1$-$C_3$haloalkyl,
$R_5$ is $C_1$-$C_4$alkyl, phenyl, or phenyl or benzyl, each substituted by one or more nitro groups, halogen atoms and/or methyl groups,
$R_4$ is the —Si($R_{11}$)($R_{12}$)($R_{13}$) group, wherein each of $R_{11}$, $R_{12}$ and $R_{13}$ independently is a radical selected from $C_1$-$C_4$alkyl, $C_3$-$C_7$alkenyl or phenyl, each unsubstituted or substituted by one or more halogen-atoms, and the agriculturally suitable acid addition salts and metal complexes thereof.

A further preferred subgroup comprises compounds of formula I, wherein X is the bridge member —CH= or —N=; Ar is a phenyl group; $R_1$ in the ortho-position is hydrogen, nitro, halogen, $C_1$-$C_3$alkyl, $C_1$-$C_3$alkoxy, or $C_1$-$C_3$haloalkyl; $R_2$ in the para-position is hydrogen, nitro, halogen, $C_1$-$C_3$alkyl, $C_1$-$C_3$alkoxy or $C_1$-$C_3$ haloalkyl; $R_3$ is hydrogen, methyl or halogen; R is a group —COOR$_5$, —COSR$_6$,

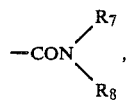

or —CN; $R_5$ is $C_1$-$C_4$alkyl, phenyl, or phenyl or benzyl, each substituted by one or more nitro groups, halogen atoms and/or methyl groups; $R_6$ is $C_1$-$C_{10}$alkyl, or phenyl or benzyl, each unsubstituted or substituted by halogen, $C_1$-$C_4$alkyl, $C_1$-$C_4$alkoxy, —CN or —CF$_3$; each of $R_7$ and $R_8$ independently is hydrogen, $C_1$-$C_3$alkyl, $C_3$-$C_7$cycloalkyl, phenyl or benzyl; and $R_4$ is the —Si($R_{11}$)($R_{12}$)($R_{13}$) group, wherein each of $R_{11}$, $R_{12}$ and $R_{13}$ independently is $C_1$-$C_4$alkyl or phenyl, each unsubstituted or substituted by halogen; and the acid addition salts and metal complexes thereof. This subgroup will be designated throughout as compounds I**.

Yet another particularly preferred subgroup comprises compounds of the formula I, wherein X is the bridge member —N=; the grouping

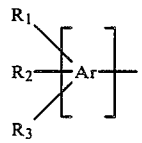

is a phenyl group which is substituted in the ortho- and/or para-position by nitro, fluorine, chlorine, bromine, methyl, methoxy and/or CF$_3$; R is the —COOR$_5$ group; $R_5$ is $C_1$-$C_4$alkyl, phenyl, or phenyl or benzyl, each substituted by nitro, chlorine, bromine, fluorine and/or methyl; and $R_4$ is the —Si($R_{11}$)($R_{12}$)($R_{13}$) group, wherein each of $R_{11}$, $R_{12}$ and $R_{13}$ independently is $C_1$-$C_4$alkyl or halophenyl, each unsubstituted or substituted by halogen; and the acid addition salts and metal complexes thereof. This subgroup will be designated throughout as compounds I***.

The following individual compounds are particularly preferred microbicides:
ethyl 2-(1H-1,2,4-triazolylmethyl-1'-yl)-2-trimethylsilyloxy-2-chloro-4-bromophenylacetate,
methyl 2-(1H-1,2,4-triazolylmethyl-1'-yl)-2-trimethylsilyloxy-2-chloro-4-bromophenylacetate,
ethyl 2-(1H-1,2,4-triazolylmethyl-1'-yl)-2-trimethylsilyloxy-2,4-dibromophenylacetate,
methyl 2-(1H-1,2,4-triazolylmethyl-1'-yl)-2-trimethylsilyloxy-2,4-dichlorophenylacetate,
ethyl 2-(1H-1,2,4-triazolylmethyl-1'-yl)-2-trimethylsilyloxy-2-chloro-4-bromophenylacetate,
methyl 2-(1H-1,2,4-triazolylmethyl-1'-yl)-2-dimethylchloromethylsilyloxy-2-chloro-4-bromophenylacetate,
ethyl 2-(1H-1,2,4-triazolylmethyl-1'-yl)-2-trimethylsilyloxy-2,4-dichlorophenylacetate,
isopropyl 2-(1H-1,2,4-triazolylmethyl-1'-yl)-2-trimethylsilyloxy-2,4-dichlorophenylacetate,
ethyl 2-(1H-1,2,4-triazolylmethyl-1'-yl)-2-dimethylallylsilyloxy-2-chloro-4-bromophenylacetate.

The compounds of the formula I are prepared by reacting an alcohol of the formula II

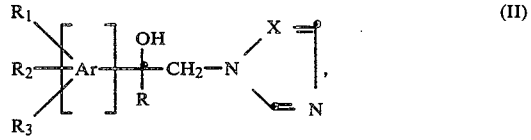

with a halosilane of the formula III

preferably in the presence of an inorganic, espcially of an organic, base, in the temperature range from −20° to +150° C., with the preferred range being from 0° to +80° C., in the absence or preferably in the presence of an inert organic solvent or diluent, and, if desired, converting the resultant compound of the formula I (e.g. Ia) into another compound of the formula I (e.g. Ib), and/or converting a free compound obtainable by the process into an acid addition salt, or converting an acid addition salt obtainable by the process into the free compound or into another acid addition salt, or converting a free compound or a salt obtainable by the process of the invention into a metal complex. In formulae II and III above, the substituents R, $R_1$, $R_2$, $R_3$, $R_4$, X and Ar are as defined for formula I, and Hal in formula III is a halogen atom, preferably a chlorine or bromine atom.

Examples of suitable solvents for the reaction are aliphatic and aromatic hydrocarbons such as benzene, toluene, xylenes, petroleum, ether; halogenated hydrocarbons such as chlorobenzene, methylene, chloride, ethylene, chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile, propionitrile; N,N-dialkylated amides such as dimethylformamide; dimethylsulfoxide; ketones such as acetone, diethyl ketone, methyl ethyl ketone; and mixtures of such solvents with one another. It can often be advantageous to carry out the reaction, or partial steps of a reaction, in an inert gas atmosphere and/or an absolute solvent. Suitable inert gases are e.g. nitrogen, helium, argon or, in certain cases, also carbon dioxide. The yield may also be improved by carrying out the reaction under elevated pressure.

Examples of suitable inorganic bases are oxides, hydrides, hydroxides, carbonates, carboxylic acid salts and alcoholates of alkaline earth metals, preferably of alkali metals, in particular those of sodium and potassium (e.g. NaH, NaOH, KOH, $Na_2CO_3$, $K_2CO_3$, $CaCO_3$, $CH_3COONa$, $C_2H_5COOK$, $C_2H_5ONa$, $CH_3ONa$ etc.), preferably the alkali metal hydrides such as NaH. Suitable organic bases are trialkylamines, e.g. triethylamine or other tertiary amines such as triethylenediamine, piperidine, pyridine, 4-dimethylaminopyridine, 4-pyrrolidylpyridine etc.

The intermediates and final products obtained by the preparatory methods of the invention can be isolated from the reaction medium and, if desired, purified by one of the methods conventionally employed, e.g. by extraction, crystallisation, chromatography, distillation etc.

Particularly advantageous variants of the process for obtaining the compounds of formula I and for preparing the intermediates, in particular those of formula II, are illustrated in two reaction schemes and subsequently described in detail.

In formulae Ia, Ib, Ic, Id, Ie, II, III, IV, V, VI, VII, VIII, IX, X, XI, XII, XIII and XIV, the substituents Ar, X, R, $R_1$, $R_2$, $R_3$, $R_4$, $R_5$, $R_6$, $R_7$ and $R_8$ are as defined for formula I.

Q in formula XV is either a customary leaving group, e.g. halogen, preferably chlorine, bromine or iodine, or is a sulfonyloxy group, preferably a benzenesulfonyloxy, paratosyloxy or lower alkylsulfonyloxy group, preferably a mesyloxy group, or is an acyloxy group such as trifluoroacetyloxy. Q is also a hydroxy group or, according to "Synthesis 1979," pp. 561-569, is the radical

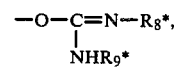

wherein $R_8{}^*$ and $R_9{}^*$ are organyl radicals, preferably lower alkyl or unsubstituted or substituted phenyl radicals. M is hydrogen or a metal atom, preferably an alkali metal atom, most preferably sodium or potassium. Hal is halogen, preferably chlorine or bromine. Y is halogen, preferably chlorine or bromine, or is a sulfate or sulfonic acid ester group.

The symbol α denotes the grouping

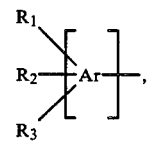

wherein the substituents $R_1$, $R_2$, $R_3$ and Ar are as defined for formula I.

Az is the following azolyl group

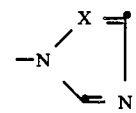

wherein X is —CH= or —N=.

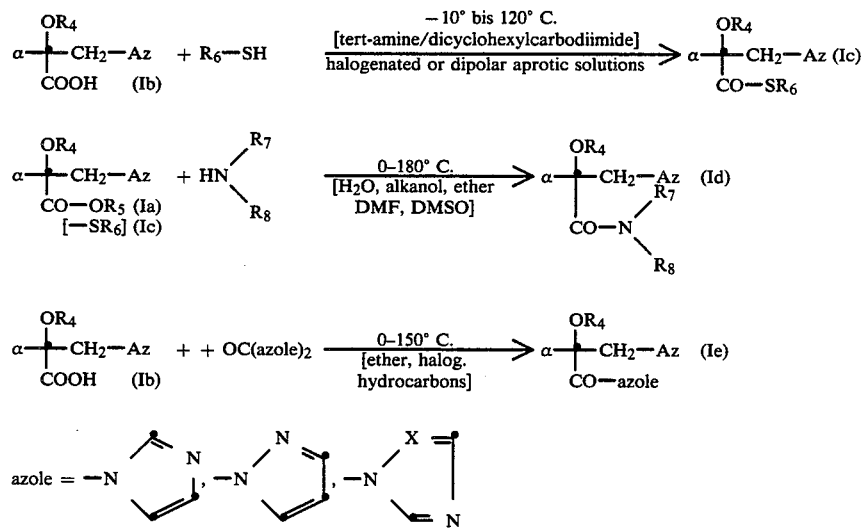

1. Reaction scheme

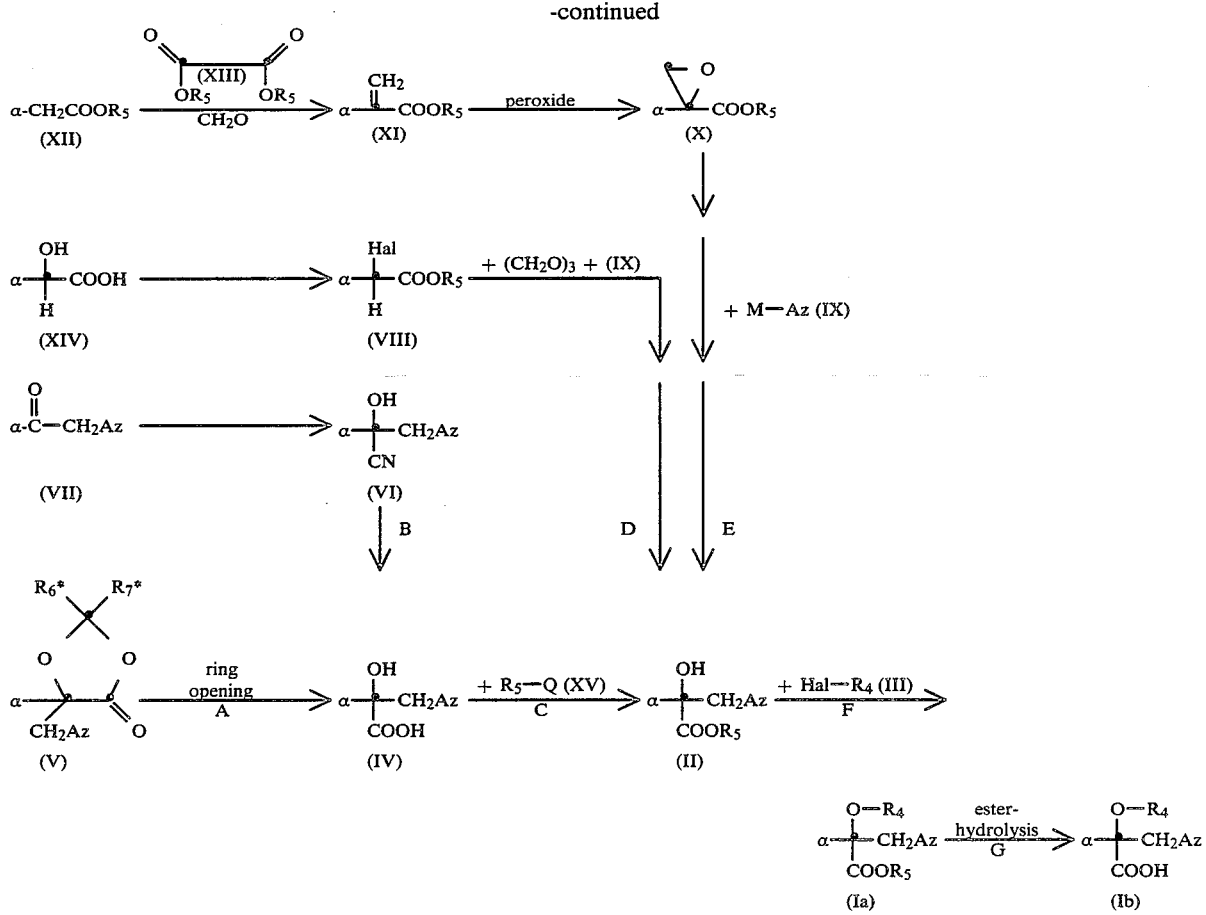

The procedure for preparing the intermediates as well as the compounds of the formula I is, in detail, as follows:

(i) Free α-hydroxycarboxylic acids of the formula IV are prepared by hydrolysing either, according to equation A, a dioxolanone of the formula V or, according to equation B, a cyanohydrin of the formula VI in basic or acid medium.

The hydrolysis reactions A and B are performed with acids or bases, advantageously in aqueous and/or alcoholic solutions, i.e. in polar solvents. The reactions can also be carried out in two-phase media, which case it is advantageous to add a customary phase-transfer catalyst. Inorganic and organic acids are suitable, e.g. mineral acids such as hydrohalic acids, sulfuric acid, phosphoric acid or sulfonic acids (p-toluenesulfonic acid, methanesulfonic acid). Suitable bases are organic and inorganic bases, e.g. oxides, hydrides, hydroxides, carbonates, carboxylic acid salts and alcoholates of alkaline earth metals and alkali metals, especially those of sodium and potassium.

The reaction temperatures for the ring opening reaction A are in general from 0° to +140° C., preferably from +30° to +80° C., and for the hydrolysis of the cyanohydrin III from +60° to +140° C. preferably from +80° to +120° C., or for both reactions at the boiling point of the solvent or solvent mixture.

Most of the starting compounds of the formula II are known from EP Published Specification No. 44276. The novel compounds are prepared by methods corresponding to those described therein.

The nitriles VI (variant B) can be prepared in conventional manner from aryl-azolylmethyl ketones of the formula VII

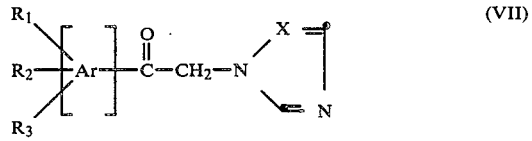

on the lines of a cyanohydrin synthesis, by reaction with HCN or an alkali cyanide, e.g. KCN or NaCN, at 0° to 100° C., advantageously in the presence of a trace of a base (preferably NH₄OH or gaseous ammonia), or by way of the corresponding NaHSO₃ adduct VII [Org. Syntheses Coll. Vol. I, p. 336, or French patent specification 2,292,706; cf. also Houben Weyl "Methoden der organischen Chemie", Vol. 6/3, p 412].

The nitriles VI can also be prepared in accordance with J. Org. Chem. 39, p. 914 (1974), by reaction of VII with trimethylsilyl cyanide, in the presence of catalytic amounts of ZnI₂, and subsequent hydrolysis of the adduct.

These nitriles may also be prepared by reaction of a ketone VII with a di-lower alkylcyanohydrin of the formula

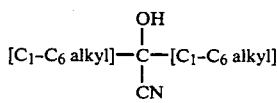

(alkyl is in particular methyl, ethyl or propyl), preferably in an inert solvent, or without a solvent, at 50°–150° C.

The hydrolysis of the nitriles VI to acid derivatives of the formula IV can be performed by methods similar to known methods, for example with concentrated hydrochloric acid [houben-Weyl "Methoden der organischen Chemie", Vol. VIII, p. 427 ff. (1952)].

Some of the ketones of formula VII used as intermediates are known from German Offenlegungsschrift No. 2 431 407 or from GB patent specification No. 1 464 224. Ketones of this type can also be obtained by hydrolysis from corresponding ketals, for example from those which are mentioned in any one of the following publications: German Offenlegungsschrift specification Nos. 2 610 022, 2 602 770, 2 930 029, 2 930 196 and 2 940 133.

Ketones of the formula VII which have not been described can be obtained by one of the aforementioned published methods.

(ii) Compound of the formula II can be prepared according to equation C, in conventional manner, by esterification of the corresponding acid derivative IV (also in the form of its alkali metal salt) with $R_5$—Q (XV) at $-20°$ to $+140°$ C. Aprotic solvents are preferred for this reaction. The direct esterification is advantageously performed with excess alcohol $R_5$—OH at 0° to 80° C. in the presence of a mineral acid, or preferably of a Lewis acid such as boron trifluoride etherate.

Compounds of the formula II can also be prepared according to equation D from an α-haloacetate of the formula VII with paraformaldehyde at 0° to 140° C., preferably at 10° to 80° C., and (a) with the desired azole of the formula IX (i.e. imidazole or triazole) in the presence of a base (e.g. NaOH), or (b) with an alkali metal salt of the azole of the formula IX in an anhydrous solvent (e.g. dimethylsulfoxide). The α-haloacetates of formula VIII can be obtained by conventional esterification of the corresponding acids XIV.

Esters of the formula II can also be prepared according to equation E from oxiranes of the formula X with an azole IX (M=H or alkali metal), in an inert, preferably polar, solvent (DMF, acetonitrile, DMSO and others, also in admixture with hydrocarbons), at 20° to 100° C. Inorganic or organic bases can be added in this reaction [cf. also EP published specification No. 15756].

As outlined in the 1st reaction scheme, oxiranes of the formula X are obtainable by customary epoxidation (for e.g. $H_2O_2$/aqueous NaOH, peracetic acid) from corresponding alkenyl compounds of the formula XI. Compounds of the formula XI are produced from arylacetates of the formula XII by reaction with oxalates of the formula XIII and formaldehyde in the presence of a base [cf. Helvetica Chimica Acta 30, p.1349 (1947) and German Offenlegungsschrift 2 653 189].

Esters of the formula II can also be prepared from acids of the formula IV and dimethylformamide acetal (preferably in excess), the acetal component of which is intended to form the alcoholic part of the ester, in a solvent (e.g. a similar anhydrous alcohol or an ether) at 0° to 160° C. [Angew. Chemie 75, p. 296 (1963) and Helv. Chim. Acta 48, 1747 (1965)].

(iii) The thioesters of the formula Ic in the 2nd reaction can be obtained from the acids Ib with thioalcohols, in the presence of weak bases (tertiary amines), in aprotic solvents such as CHCl$_3$, DMF, dichloromethane, DMSO, at $-10°$ to $+120°$ C., preferably at 0° to $+40°$ C. Corresponding mandelic acid amides and mandelic acid hydrazides Id are obtainable from esters (or thioesters) of the formula Ia with excess amine R$_7$—N—H—R$_8$. When R$_7$ and R$_8$ are closed to form a 5- or 6-membered ring, as in the case of compounds of formula Ie, a heterocycle of this kind is introduced advantageously by reaction of the acid Ib with 1,1'-carbonyldiazole or -diazine at 0° to 150° C., preferably in a solvent such as an ether or a halogenated hydrocarbon.

(iv) The free hydroxyl group in compounds IV and II is, as described above, subjected to silylation with halosilanes of the formula III.

The other starting compounds of formulae III, IX, XII, XIII and XV are known or they can be obtained by methods which are known per se.

The compounds of formula I

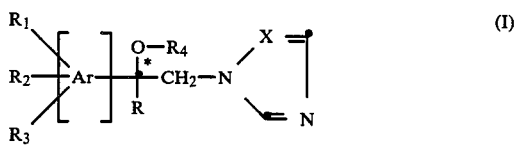

contain a centre of asymmetry (*) vicinal to the aromatic group Ar and to R, and can therefore be obtained in the form of two enantiomers. In general, a mixture of both enantiomers is obtained in the preparation of these compounds. This mixture can be resolved into the optical antipodes in conventional manner. Optically pure antipodes are obtained e.g. in variant B, in which the racemate of the formula IV is converted e.g. with an optically active base into the corresponding salts, which are separated by fractional crystallisation and from which the optically pure acids of the formula IV are obtained. These acids can be converted, as illustrated in variant C, into the optically pure esters of the formula II, which in turn can be converted, as in variant F, into the silylated esters Ia.

Unless otherwise specifically mentioned, reference to a compound of formula I will always be intended to mean a mixture of both enantiomers. Both antipodes have different microbicidal properties.

Surprisingly, it has been found that compounds of the formula I have for practical purposes a very useful microbicidal spectrum against phytopathogenic fungi and bacteria. They have very valuable curative, preventive and systemic properties and can be used for protecting cultivated plants. With the compounds of the formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Ascomycetes (e.g. Venturia, Podosphaera, Erysiphe, Monilinia, Uncinula); Basidomycetes (e.g. the genera Hemileia, Rhizoctonia, Pellicularia, Puccinia); Fungi imperfecti (e.g. Botyrtis, Helminthosporium, Fusarium, Septoria, Cercospora, Piricularia and Alternaria). In addition, the compounds of formula I have a systemic action. They can also be used as seed dressing agents for protecting seeds (fruit, tubers, grains) and plant cuttings against fungus infections as well as against phytopathogenic microorganisms which occur in the soil. The compounds of the invention are also especially well tolerated by plants.

Accordingly, the invention also relates to microbicidal compositions and to the use of compounds of the formula I for controlling phytophatogenic microorganisms, especially parasitic fungi, and for the preventive treatment of plants to protect them from attack by such microorganisms.

The invention further embraces the preparation of agrochemical compositions which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these prepartions, if desired together with further carriers, surfactants or application-promoting adjuvants customarily employed in the art of formulation. Particularly advantageous adjuvants are phospholipids of vegetable or animal origin. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

The compounds of the formula I are used in unmodified form or, preferably, together with the adjuvants conventionally employed in the art of formulation, and are therefore formulated in known manner to emulsifiable concentrates, coatable pastes, directly sprayable to dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha. The application of such compositions can be made direct to the plant or parts thereof (foliar application), or to the locus of the plant (soil application), or to the propagation parts, e.g. by seed application.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used. e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 1 to 99.9%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

EXAMPLE 1

Preparation of

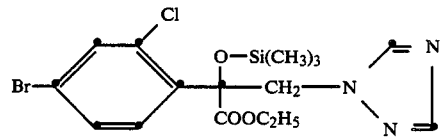

Ethyl 2-(1H-1,2,4-triazolylmethyl-1′-yl)-2-trimethylsilyloxy-2-chloro-4-bromophenylacetate:

A solution of 3.6 g (0.033 mole) of trimethylchlorosilane in 20 ml of dichloromethane is added dropwise, at room temperature, to 11.2 g (0.03 mole) of diethyl 2-(1H-1,2,4-triazolylmethyl-1′-yl)-2-hydroxy-2-chloro-4-bromophenylacetate and 3.6 g (0.036 mole) of triethylamine in 50 ml of dichloromethane. The reaction mixture is then stirred for 16 hours at room temperature, subsequently washed in succession with sodium carbonate solution and with water, and the dichloromethane phase is dried over sodium sulfate and filtered. The solvent is removed in vacuo, affording 12 g of the title compound in the form of a brown resin.

The following compounds of this invention can be prepared in accordance with the procedure of this Example and with the process variants described hereinbefore.

TABLE 1

Compounds of the formula

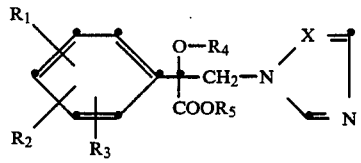

| Compound | $R_1$ | $R_2$ | $R_3$ | $R_4$ | $R_5$ | X | Physical data (°C.) |
|---|---|---|---|---|---|---|---|
| 1.1 | 2-Cl | 4-Br | H | —Si(CH$_3$)$_3$ | CH$_3$ | N | $n_D^{42}$ 1.5240 |
| 1.2 | 2-Cl | 4-Br | H | —Si(CH$_3$)$_3$ | CH$_3$ | CH | |
| 1.3 | 2-Cl | 4-Br | H | —Si(CH$_3$)$_3$ | C$_2$H$_5$ | N | $n_D^{36}$ 1.5390 |
| 1.4 | 2-Cl | 4-Br | H | —Si(CH$_3$)$_3$ | C$_3$H$_7$—n | N | |
| 1.5 | 2-Cl | 4-Br | H | —Si(CH$_3$)$_3$ | C$_3$H$_7$—i | N | |
| 1.6 | 2-Cl | 4-Br | H | —Si(CH$_3$)$_3$ | C$_4$H$_9$—n | N | |
| 1.7 | 2-Cl | 4-Br | H | —Si(CH$_3$)$_3$ | Cyclopentyl | N | |
| 1.8 | 2-Cl | 4-Br | H | —Si(CH$_3$)$_3$ | CH$_2$—C$_6$H$_5$ | N | $n_D^{37}$ 1.5330 |

TABLE 1-continued

Compounds of the formula

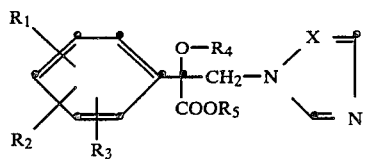

| Compound | R₁ | R₂ | R₃ | R₄ | R₅ | X | Physical data (°C.) |
|---|---|---|---|---|---|---|---|
| 1.9 | 2-Cl | 4-Br | H | —Si(CH₃)₃ | CH₂CH₂Cl | N | |
| 1.10 | 2-Cl | 4-Br | H | —Si(CH₃)₃ | CH₂CH₂OCH₃ | N | |
| 1.11 | 2-Cl | 4-Br | H | —Si(CH₃)₃ | CH₂CH=CH₂ | N | |
| 1.12 | 2-Cl | 4-Br | H | —Si(CH₃)₃ | CH₂OCH₃ | N | |
| 1.13 | 2-Cl | 4-Br | H | —Si(CH₃)₃ | CH₂SCH₃ | N | |
| 1.14 | 2-Cl | 4-Br | H | —Si(CH₃)₃ | CH₂COOC₂H₅ | N | |
| 1.15 | 2-Cl | 4-Br | H | —Si(CH₃)₃ | CH(CH₃)COOCH₃ | N | |
| 1.16 | 2-Cl | 4-Br | H | —Si(CH₃)₃ | CH₂C(O)C₄H₉—t | N | |
| 1.17 | 2-Cl | 4-Br | H | —Si(C₂H₅)₃ | CH₃ | N | m.p. 87–94° |
| 1.18 | 2-Cl | 4-Br | H | —Si(C₂H₅)₃ | CH₂CH₂Cl | N | |
| 1.19 | 2-Cl | 4-Br | H | —Si(CH₃)₂CH₂Cl | CH₃ | N | m.p. 100–2° |
| 1.20 | 2-Cl | 4-Br | H | —Si(CH₃)₂CH₂Cl | C₂H₅ | N | $n_D^{42}$ 1.5315 |
| 1.21 | 2-Cl | 4-Br | H | —Si(CH₃)₂C₄H₉—t | C₂H₅ | N | $n_D^{40}$ 1.5201 |
| 1.22 | 2-Cl | 4-Br | H | —Si(CH₃)₂CH₂CH=CH₂ | C₂H₅ | N | $n_D^{43}$ 1.5373 |
| 1.23 | 2-Cl | 4-Br | H | —Si(C₆H₅)₂C₄H₉—t | C₂H₅ | N | m.p .131–9° |
| 1.24 | 2-Cl | 4-Br | H | —Si(C₆F₅)(CH₃)₂ | C₂H₅ | N | $n_D^{42}$ 1.5161 |
| 1.25 | 2-Br | 4-Br | H | —Si(CH₃)₃ | C₂H₅ | N | $n_D^{36}$ 1.5420 |
| 1.26 | 2-Br | 4-Br | H | —Si(C₂H₅)₃ | C₂H₅ | N | |
| 1.27 | H | 4-Br | H | —Si(CH₃)₃ | C₂H₅ | N | |
| 1.28 | 2-Cl | 4-F | H | —Si(CH₃)₃ | CH₃ | N | |
| 1.29 | 2-Cl | 4-F | H | —Si(CH₃)₃ | CH₃ | CH | |
| 1.30 | 2-Cl | 4-F | H | —Si(CH₃)₃ | C₂H₅ | N | |
| 1.31 | 2-Cl | 4-F | H | —Si(C₂H₅)₃ | CH₃ | N | |
| 1.32 | 2-Cl | 4-Cl | H | —Si(CH₃)₃ | CH₃ | N | m.p. 86–87° |
| 1.33 | 2-Cl | 4-Cl | H | —Si(CH₃)₃ | CH₃ | CH | |
| 1.34 | 2-Cl | 4-Cl | H | —Si(CH₃)₃ | C₂H₅ | N | m.p. 104–5° |
| 1.35 | 2-Cl | 4-Cl | H | —Si(CH₃)₃ | C₃H₇—n | N | m.p. 60–61° |
| 1.36 | 2-Cl | 4-Cl | H | —Si(CH₃)₃ | C₃H₇—i | N | m.p. 107–8° |
| 1.37 | 2-Cl | 4-Cl | H | —Si(CH₃)₃ | C₄H₉—n | N | $n_D^{54}$ 1.5040 |
| 1.38 | 2-Cl | 4-Cl | H | —Si(CH₃)₃ | C₄H₉—t | N | |
| 1.39 | 2-Cl | 4-Cl | H | —Si(CH₃)₃ | cyclohexyl | N | $n_D^{54}$ 1.5161 |
| 1.40 | 2-Cl | 4-Cl | H | —Si(CH₃)₃ | cyclopentyl | N | |
| 1.41 | 2-Cl | 4-Cl | H | —Si(CH₃)₃ | C₆H₅ | N | |
| 1.42 | 2-Cl | 4-Cl | H | —Si(CH₃)₃ | CH₂C₆H₅ | N | |
| 1.43 | 2-Cl | 4-Cl | H | —Si(CH₃)₃ | CH₂CH₂Cl | N | |
| 1.44 | 2-Cl | 4-Cl | H | —Si(CH₃)₃ | CH₂CH₂OCH₃ | N | |
| 1.45 | 2-Cl | 4-Cl | H | —Si(CH₃)₃ | CH₂CH=CH₂ | N | m.p. 58–59° |
| 1.46 | 2-Cl | 4-Cl | H | —Si(CH₃)₃ | CH₂OCH₃ | N | |
| 1.47 | 2-Cl | 4-Cl | H | —Si(CH₃)₃ | CH₂SCH₃ | N | |
| 1.48 | 2-Cl | 4-Cl | H | —Si(CH₃)₃ | CH₂COOC₂H₅ | N | $n_D^{54}$ 1.511 |
| 1.49 | 2-Cl | 4-Cl | H | —Si(CH₃)₃ | CH(CH₃)COOCH₃ | N | |
| 1.50 | 2-Cl | 4-Cl | H | —Si(CH₃)₃ | CH₂C(O)C₄H₉—t | N | |
| 1.51 | 2-Cl | 4-Cl | H | —Si(C₂H₅)₃ | CH₃ | N | m.p. 107–8° |
| 1.52 | 2-Cl | 4-Cl | H | —Si(C₂H₅)₃ | C₂H₅ | N | |
| 1.53 | 2-Cl | 4-Cl | H | —Si(C₂H₅)₃ | C₃H₇—i | N | $n_D^{54}$ 1.4910 |
| 1.54 | 2-Cl | 4-Cl | H | —Si(C₂H₅)₃ | C₄H₉—n | N | |
| 1.55 | 2-Cl | 4-Cl | H | —Si(C₂H₅)₃ | CH₂CH=CH₂ | N | |
| 1.56 | 2-Cl | 4-Cl | H | —Si(CH₃)₂CH₂Cl | CH₃ | N | |
| 1.57 | 2-Cl | 4-Cl | H | —Si(CH₃)₂C₄H₉—t | CH₃ | N | |
| 1.58 | 2-Cl | 4-Cl | H | —Si(CH₃)₂CH₂CH=CH₂ | CH₃ | N | |
| 1.59 | 2-Cl | 4-Cl | H | —Si(C₆H₅)₂C₄H₉—t | CH₃ | N | |
| 1.60 | 2-Cl | 4-Cl | H | —Si(CH₃)₂C₆F₅ | CH₃ | N | |
| 1.61 | 2-Cl | 4-Cl | 6-Cl | —Si(CH₃)₃ | C₂H₅ | N | |
| 1.62 | 2-Cl | 4-Cl | H | —Si(CH₃)₂C₆H₅ | CH₃ | N | |
| 1.63 | 2-Cl | 4-Cl | H | —Si(C₆H₅)₂CH₃ | CH₃ | N | |
| 1.64 | 2-Cl | 4-Br | H | —Si(CH₃)₂C₆H₅ | C₂H₅ | N | $n_D^{40}$ 1.5460 |
| 1.65 | 2-Cl | 4-Br | H | —Si(C₆H₅)₂CH₃ | C₂H₅ | N | |
| 1.66 | 2-Cl | 4-Br | H | —Si(C₂H₅)₃ | C₂H₅ | N | $n_D^{43}$ 1.5222 |
| 1.67 | 2-Br | 4-Br | H | —Si(CH₃)₃ | C₃H₇—i | N | m.p. 92–96° |

TABLE 2

Compounds of the formula

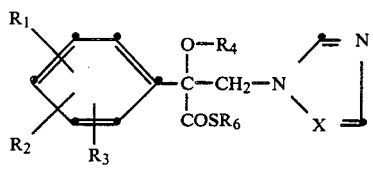

| Compound | R₁ | R₂ | R₃ | R₄ | R₆ | X | Physical data (°C.) |
|---|---|---|---|---|---|---|---|
| 2.1 | 2-Cl | 4-Cl | H | —Si(CH₃)₃ | CH₃ | N | |
| 2.2 | 2-Cl | 4-Cl | H | —Si(CH₃)₃ | C₂H₅ | N | m.p. 88–90° |
| 2.3 | 2-Cl | 4-Cl | H | —Si(CH₃)₃ | C₂H₅ | CH | |
| 2.4 | 2-Cl | 4-Cl | H | —Si(CH₃)₃ | CH₂C₆H₅ | N | |
| 2.5 | 2-Cl | 4-Cl | H | —Si(CH₃)₃ | C₆H₅ | N | |
| 2.6 | 2-Cl | 4-Cl | H | —Si(C₂H₅)₃ | CH₃ | N | |
| 2.7 | 2-Cl | 4-Cl | H | —Si(C₂H₅)₃ | C₂H₅ | N | |
| 2.8 | 2-Cl | 4-Cl | H | —Si(CH₃)₂CH₂Cl | C₂H₅ | N | |
| 2.9 | 2-Cl | 4-Br | H | —Si(CH₃)₃ | C₂H₅ | N | |
| 2.10 | 2-Cl | 4-Br | H | —Si(C₂H₅)₃ | C₂H₅ | N | |
| 2.11 | 2-Cl | 4-F | H | —Si(CH₃)₃ | C₂H₅ | N | |
| 2.12 | 2-Cl | 4-F | H | —Si(C₂H₅)₃ | C₂H₅ | N | |
| 2.13 | 2-Cl | 4-Cl | 6-Cl | —Si(CH₃)₃ | C₂H₅ | N | |

TABLE 3

Compounds of the formula

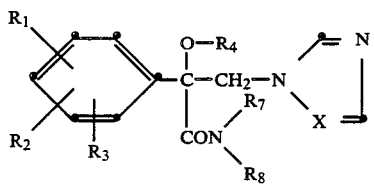

| Compound | R₁ | R₂ | R₃ | R | —N(R₇)(R₈) | X | Physical data (°C.) |
|---|---|---|---|---|---|---|---|
| 3.1 | 2-Cl | 4-Cl | H | —Si(CH₃)₃ | —N(CH₃)₂ | N | |
| 3.2 | 2-Cl | 4-Cl | H | —Si(CH₃)₃ | —NHCH₃ | N | |
| 3.3 | 2-Cl | 4-Cl | H | —Si(CH₃)₃ | —NHCH₃ | CH | |
| 3.4 | 2-Cl | 4-Cl | H | —Si(CH₃)₃ | —N(pyrazole) | N | |
| 3.5 | 2-Cl | 4-Cl | H | —Si(CH₃)₃ | —N(triazole) | N | |
| 3.6 | 2-Cl | 4-Cl | H | —Si(C₂H₅)₃ | —NHCH₃ | N | |
| 3.7 | 2-Cl | 4-F | H | —Si(CH₃)₃ | —N(CH₃)₂ | CH | |
| 3.8 | 2-Cl | 4-F | H | —Si(CH₃)₃ | —NHCH₃ | N | |
| 3.9 | 2-Cl | 4-F | H | —Si(CH₃)₃ | NHCH₂C₆H₅ | N | |
| 3.10 | 2-Cl | 4-Cl | 6-Cl | —Si(C₂H₅)₃ | —N(CH₃)₂ | N | |
| 3.11 | 2-Cl | 4-Br | H | —Si(CH₃)₃ | —N(CH₃)₂ | N | |
| 3.12 | 2-Cl | 4-Br | H | —Si(CH₃)₃ | —NHCH₃ | N | |
| 3.13 | 2-Cl | 4-Br | H | —Si(CH₃)₃ | —NHC₂H₅ | N | |
| 3.14 | 2-Cl | 4-Br | H | —Si(CH₃)₃ | —NHN(CH₃)₂ | N | |

TABLE 4

Compounds of the formula

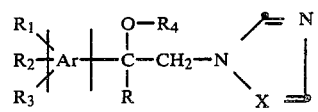

| Compound | $R_1, R_2, R_3 \text{—Ar—}$ | $R_4$ | R | X | Physical data (°C.) |
|---|---|---|---|---|---|
| 4.1 | biphenyl | —Si(CH$_3$)$_3$ | —COOCH$_3$ | N | |
| 4.2 | 4-chlorobiphenyl | —Si(CH$_3$)$_3$ | —COOCH$_3$ | N | |
| 4.3 | 6-methylnaphth-2-yl | —Si(CH$_3$)$_3$ | —COOCH$_3$ | N | |
| 4.4 | 6-chloronaphth-2-yl | —Si(CH$_3$)$_3$ | —COOCH$_3$ | CH | |
| 4.5 | naphth-2-yl | —Si(CH$_3$)$_3$ | —COOCH$_3$ | N | |

FORMULATION EXAMPLES

Formulation Examples for active ingredients of the formula I (throughout, percentages are by weight):

| A Emulsifiable concentrates | a | b | c |
|---|---|---|---|
| a compound of tables 1 to 4 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| B Solutions | a | b | c | d |
|---|---|---|---|---|
| a compound of tables 1 to 4 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20 | — | — |
| epoxidised coconut oil | — | — | 1% | 5% |
| petroleum distillate (boiling range 160–190°) | — | — | 94% | — |

These solutions are suitable for application in the form of microdrops.

| C Granulates | a | b |
|---|---|---|
| a compound of tables 1 to 4 | 5% | 10% |
| kaolin | 94% | — |
| highly dispersed silicic acid | 1% | — |

-continued

| C Granulates | a | b |
|---|---|---|
| attapulgite | — | 90% |

The active ingredient is dissolved in methylene chloride, the solution is sprayed onto the carrier, and the solvent is subsequently evaporated off in vacuo.

| D Dusts | a | b |
|---|---|---|
| a compound of tables 1 to 4 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| E Wettable powders | a | b | c |
|---|---|---|---|
| a compound of tables 1 to 4 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

BIOLOGICAL EXAMPLES

EXAMPLE B1

Action against *Puccinia graminis* on wheat:
(a) Residual-protective action:
Wheat plants are treated 6 days after sowing with a spray mixture prepared from a wettable powder formulation of the active ingredient (0.06%). After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.
(b) Systemic action:
Wheat plants are treated 5 days after sowing with a spray mixture prepared from a wettable powder formulation of the active ingredient (0.006% based on the volume of the soil). After 48 hours the treated plants are infected with a uredospore suspension of the fungus. The plants are then incubated for 48 hours at 95-100% relative humidity and about 20° C. and then stood in a greenhouse at about 22° C. Evaluation of rust pustule development is made 12 days after infection. Attack on untreated and infected control plants is 100%. Plants treated with compositions containing compounds of formula I exhibit only insignificant (<20%) or no attack. Compounds 1.1, 1.3, 1.8, 1.17, 1.19 to 1.25, 1.32, 1.34 to 1.37, 1.39, 1.45, 1.48. 1.51, 1.53, 1.64, 1.66 and 1.67 completely inhibit fungus attack (0-5%). Compound 1.1 still inhibits fungus attack completely even when used in a concentration of 0.002%.

EXAMPLE B2

Action against *Cercospora arachidicola* in groundnut plants:
Residual protective action:
Groundnut plants 10-15 cm in height are sprayed with a wettable powder containing 0.006% of active ingredient and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection, and is based on the number and size of the specks.
Compared with untreated and infected control plants (number and size of specks=100%), cercospora attack is significantly reduced on groundnut plants treated with compounds of Tables 1 to 4. For example; compounds 1.1, 1.3, 1.8, 1.19, 1.20, 1.22, 1.24, 1.25, 1.32, 1.34 to 1.37, 1.39, 1.45, 1.53, 1.64, 1.66 and 1.67 and others inhibit the occurrence of specks almost completely (0-10%) in the above tests.

EXAMPLE B3

Action against *Erysiphe graminis on barley:*
(a) Residual protective action:
Barley plants about 8 cm in height are sprayed with a spray mixture (0.02%) prepared from the active ingredient formulated as a wettable powder. The treated plants are dusted with conidia of the fungus after 3-4 hours. The infected barley plants are then stood in a greenhouse at about 22° C. The extent of the infestation is evaluated after 10 days.
(b) Systemic action:
Barley plants about 8 cm in height are treated with a spray mixture (0.006%, based on the volume of the soil) prepared from the active ingredient formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days. Compounds of formula I and compounds of Tables 1 to 4 reduce fungus attack to less than 20%, whereas attack is 100% on untreated and infected control plants. Compounds 1.1, 1.3, 1.8, 1.17, 1.19, 1.20, 1.21, 1.22, 1.24, 1.25, 1.32, 1.34 to 1.37, 1.45, 1.48, 1.51, 1.53, 1.64, 1.66 and 1.67 and others inhibit fungus attack completely (0-5%).

EXAMPLE B4

Residual-protective action against *Venturia inaequalis* on apple shoots:
Apple cuttings with 10-20 cm long fresh shoots are sprayed with a spray mixture prepared from a wettable powder formulation of the active ingredient with a conidia suspension of the fungus. The plants are then incubated for 5 days at 90-100% relative humidity and stood in a greenhouse for a further 10 days at 20°-24° C. Scab infestation is evaluated 15 days after infection. Compounds 1.3, 1.8 and 1.25 and others inhibit infestation to less than 10% and completely (e.g. compound 1.3). Shoots on apple trees in field trials are protected to the same extent without being inhibited in their development.

EXAMPLE B5

Action against *Botrytis cinerea* on beans:
Residual protective action:

Bean plants about 10 cm in height are sprayed with a spray mixture (0.02% concentration) prepared from the active ingredient formulated as wettable powder. After 48 hours, the treated plants are infected with a conidia suspension of the fungus. The infected plants are incubated for 2 to 3 days at 95-100% relative humidity and 21° C., and evaluation of the fungus attack is then made. Comounds of Tables 1 to 4 inhibit fungus infection very strongly in many cases. At a concentration of 0.02%, compounds 1.1, 1.3, 1.8, 1.19, 1.20, 1.21, 1.22, 1.24, 1.25, 1.32, 1.34, 1.35, 1.36, 1.37, 1.39, 1.45, 1.66 and 1.67 are fully effective (attack 0-5%).

EXAMPLE B6

Action against Piricularia on rice:
Residual-protective action:

After being reared for 2 weeks, rice plants are sprayed with a spray mixture (0.02%) prepared from a wettable powder formulation of the test compound. The treated plants are infected 48 hours later with a conidia suspension of the fungus. Fungus attack is evaluated after incubation for 5 days at 95-100% relative humidity and 24° C. Compared with 100% attack on unprotected plants, compounds of Tables 1 to 4 inhibit fungus infestation significantly, e.g. compounds 1.1, 1.8, 1.19, 1.20, 1.22, 1.24, 1.25, 1.35 and 1.66.

What is claimed is:

1. A compound of the formula

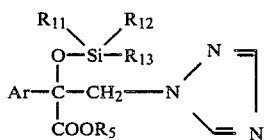

wherein

Ar is phenyl substituted in the ortho- and/or para-position by nitro, fluorine, chlorine, bromine, methyl, methoxy or trifluoromethyl, $R_5$ is $C_1-C_4$ alkyl, phenyl, benzyl, or phenyl or benzyl substituted by nitro, chlorine, bromine, fluorine or methyl, and each of $R_{11}$, $R_{12}$ and $R_{13}$ is $C_1-C_4$ or phenyl, each optionally substituted by halogen, or an acid addition salt or metal complex thereof.

2. A compound according to claim 1, selected from the group consisting of:

ethyl 2-(1H-1,2,4-triazolylmethyl-1'-yl)-2-trimethylsilyloxy-2-chloro-4-bromophenylacetate, methyl 2-(1H-1,2,4-triazolylmethyl-1'-yl)-2-trimethylsilyloxy-2-chloro-4-bromophenylacetate, ethyl 2-(1H-1,2,4-triazolylmethyl-1'-yl)-2-trimethylsilyloxy-2,4-dibromophenylacetate, methyl 2-(1H-1,2,4-triazolylmethyl-1'-yl)-2-trimethylsilyloxy-2,4-dichlorophenylacetate, ethyl 2-(1H-1,2,4-triazolylmethyl-1'-yl)-2-trimethylsilyloxy-2-chloro-4-bromophenylacetate, methyl 2-(1H-1,2,4-triazolylmethyl-1'-yl)-2-dimethylchloromethylsilyloxy-2-chloro-4-bromophenylacetate, ethyl 2-(1H-1,2,4-triazolylmethyl-1'-yl)-2-trimethylsilyloxy-2,4-dichlorophenylacetate, isopropyl 2-(1H-1,2,4-triazolylmethyl-1'-yl)-2-trimethylsilyloxy-2,4-dichlorophenylacetate, and ethyl 2-(1H-1,2,4-triazolylmethyl-1'-yl)-2-dimethylallylsilyloxy-2-chloro-4-bromophenylacetate.

3. A metal complex of a compound according to claim 1 with copper, zinc, manganese or tin.

4. A pesticidal composition for controlling or preventing infestation by parasitic microorganisms, which composition contains as active ingredient a pesticidally effective amount of a compound as claimed in claim 1, together with suitable carriers therefor.

5. The compound according to claim 2 which is ethyl 2-(1H-1,2,4-trizolylmethyl-1'-yl)-2-trimethylsilyloxy-2-chloro-4-bromophenylacetate.

6. The compound according to claim 2 which is methyl 2-(1H-1,2,4-triazolylmethyl-1'-yl)-2-trimethylsilyloxy-2,4-dichlorophenylacetate.

7. The compound according to claim 2 which is isopropyl 2-(1H-1,2,4-triazolylmethyl-1'-yl)-2-trimethylsilyloxy-2,4-dichlorophenylacetate.

8. A method of controlling phytopathogenic microorganisms or of protecting cultivated plants from attack by such microorganisms, which comprises applying to said plants or to the locus thereof a microbicidally effective amount of a compound as claimed in claim 1.

* * * * *